(12) United States Patent
Schramm et al.

(10) Patent No.: US 6,850,592 B2
(45) Date of Patent: Feb. 1, 2005

(54) METHODS FOR IDENTIFICATION AND VERIFICATION USING DIGITAL EQUIVALENT DATA SYSTEM

(75) Inventors: Harry F. Schramm, Winchester, TN (US); Bruce Kaiser, Draper, UT (US); Robert D. Kuhlman, Richland, WA (US); Therese Howe, Kennewick, WA (US); Robert Shannon, Burbank, WA (US); Ken Wheeler, Kennewick, WA (US)

(73) Assignee: Keymaster Technologies, Inc., Kennewick, WA (US)

( * ) Notice: Subject to any disclaimer, the term of this patent is extended or adjusted under 35 U.S.C. 154(b) by 23 days.

(21) Appl. No.: 10/321,873

(22) Filed: Dec. 16, 2002

(65) Prior Publication Data

US 2003/0194053 A1 Oct. 16, 2003

Related U.S. Application Data

(63) Continuation-in-part of application No. 10/122,079, filed on Apr. 12, 2002.

(51) Int. Cl.⁷ ............................................. G01N 23/223
(52) U.S. Cl. .......................................... 378/45; 162/57
(58) Field of Search ............................ 378/45, 42, 57, 378/162, 163, 1; 250/271, 358.1; 235/494

(56) References Cited

U.S. PATENT DOCUMENTS

| | | |
|---|---|---|
| 2,957,079 A | 10/1960 | Edholm |
| 4,045,676 A | 8/1977 | Rolle |
| 4,136,778 A | 1/1979 | Wortman et al. |
| 4,251,726 A | 2/1981 | Alvarez |
| 4,363,965 A | 12/1982 | Soberman et al. |
| 4,390,452 A * | 6/1983 | Stevens .................. 252/408.1 |
| 4,445,225 A | 4/1984 | White |
| 4,476,382 A | 10/1984 | White |
| 4,485,308 A | 11/1984 | Rabatin |
| 4,767,205 A | 8/1988 | Schwartz et al. |

(List continued on next page.)

FOREIGN PATENT DOCUMENTS

| | | |
|---|---|---|
| EP | 011627 A1 | 10/1998 |
| EP | 0 911 626 A1 | 10/1998 |
| EP | 0 911 627 A1 | 10/1998 |
| WO | WO0125747 | 4/2001 |
| WO | WO0125748 | 4/2001 |

(List continued on next page.)

OTHER PUBLICATIONS

Kaiser et al., PCT application No. PCT/US02/05219, published as WO 02/068945 on Sep. 6, 2002 includng U.S. application No. 10/006,782, claiming priority thereof.
Kaiser et al., PCT application No. PCT/US00/26415, published as WO 01/25820 on Apr. 12, 2001.
Kaiser et al., PCT application No. PCT/US00/26461, published as WO 01/25763 on Apr. 12, 2001.

(List continued on next page.)

Primary Examiner—Craig E. Church
Assistant Examiner—Irakli Kiknadze
(74) Attorney, Agent, or Firm—Kenneth E. Horton; Kirton & McConkie (57) ABSTRACT

Apparatus and methods in which one or more elemental taggants that are extrinsically placed in an object are detected by x-ray fluorescence analysis to identify or authenticate the object are described. The taggant is manufactured as part of the object or the taggant is placed into a coating, packaging, label, or otherwise embedded onto the object for the purpose of later verifying the presence or absence of these elements by x-ray fluorescence. The taggant is then analyzed by XRF and the analysis is then converted into a 2D symbol format that can be used in various security and authentication applications. By using x-ray fluorescence analysis, the apparatus and methods of the invention are simple and easy to use, without the limitations experience by current anti-counterfeiting technologies.

22 Claims, 9 Drawing Sheets

U.S. PATENT DOCUMENTS

| | | | |
|---|---|---|---|
| 4,862,143 A | | 8/1989 | Hirshfield et al. |
| 5,057,268 A | | 10/1991 | Muller |
| 5,185,773 A | | 2/1993 | Blossfeld et al. |
| 5,208,630 A | | 5/1993 | Goodbrand et al. |
| 5,301,044 A | | 4/1994 | Wright |
| 5,461,654 A | | 10/1995 | Grodzins et al. |
| 5,474,937 A | | 12/1995 | Anderson, II et al. |
| 5,527,707 A | | 6/1996 | Fukazawa |
| 5,670,239 A | | 9/1997 | Hampp |
| 5,677,187 A | | 10/1997 | Anderson, II et al. |
| 5,692,029 A | * | 11/1997 | Husseiny et al. ............ 378/88 |
| 5,740,223 A | | 4/1998 | Ozawa et al. |
| 5,760,394 A | | 6/1998 | Welle |
| 5,830,769 A | | 11/1998 | Wieder et al. |
| 5,849,590 A | | 12/1998 | Anderson, II et al. |
| 6,005,915 A | | 12/1999 | Hossain et al. |
| 6,007,744 A | | 12/1999 | Nacker |
| 6,024,200 A | | 2/2000 | Jang |
| 6,025,200 A | | 2/2000 | Kaish et al. |
| 6,030,657 A | | 2/2000 | Butland et al. |
| 6,041,095 A | | 3/2000 | Yokhin |
| 6,075,839 A | | 6/2000 | Treseder |
| 6,082,775 A | | 7/2000 | Phillips |
| 6,088,423 A | * | 7/2000 | Krug et al. ................ 378/57 |
| 6,097,785 A | | 8/2000 | Elam |
| 6,106,021 A | | 8/2000 | Phillips |
| 6,111,929 A | | 8/2000 | Hazlett |
| 6,130,931 A | | 10/2000 | Laurila et al. |
| 6,165,609 A | | 12/2000 | Curatolo |
| 6,178,226 B1 | | 1/2001 | Hell et al. |
| 6,178,227 B1 | | 1/2001 | Sato |
| 6,200,628 B1 | | 3/2001 | Rozumek et al. |
| 6,313,423 B1 | | 11/2001 | Sommer et al. |
| 6,456,729 B1 | * | 9/2002 | Moore ....................... 382/103 |
| 6,477,227 B1 | | 11/2002 | Kaiser et al. |
| 6,501,825 B2 | | 12/2002 | Kaiser et al. |
| 6,533,181 B1 | * | 3/2003 | Roxby et al. ............... 235/494 |
| 6,563,902 B2 | | 5/2003 | Takahashi |
| 6,685,095 B2 | * | 2/2004 | Roustaei et al. ....... 235/472.01 |

FOREIGN PATENT DOCUMENTS

| | | |
|---|---|---|
| WO | WO0125763 | 4/2001 |
| WO | WO0125764 | 4/2001 |
| WO | WO0125765 | 4/2001 |
| WO | WO0125766 | 4/2001 |
| WO | WO0125767 | 4/2001 |
| WO | WO0125768 | 4/2001 |
| WO | WO0125820 | 4/2001 |
| WO | WO0125821 | 4/2001 |
| WO | WO0250570 | 6/2002 |
| WO | WO0268945 | 9/2002 |

OTHER PUBLICATIONS

Kaiser et al., PCT application No. PCT/US00/16784, published as WO 01/025764 on Apr. 12, 2001.

Kaiser et al., PCT application No. PCT/US00/27482, published as WO 02/50570 on Jun. 27. 2002.

Kaiser et al., PCT application No. PCT/US00–27491, published as WO 01/25767 on Apr. 12, 2001 including U.S. application No. 10/089,671, claiming priority thereof.

Kaiser et al., PCT application No. PCT/US00/27624, published as WO 01/25821 on Apr. 12, 2001 including U.S. application No. 10/089,872, claiming priority thereof.

Kaiser et al., PCT application No. PCT/US00/27423, published as WO 01/025748 on Apr. 12, 2001 including U.S. application No. 10/089,670, claiming priority thereof.

Kaiser et al., PCT application No. PCT/US00/27420, published as WO 01/025766 on Apr. 12, 2001 including U.S. application No. 10/089,671, claiming priority thereof.

Kaiser et al., PCT application No. PCT/US00/27151, published as WO 01/25765 on Apr. 12, 2001.

Kaiser et al., PCT application No. PCT/US00/27492, published as WO 01/025768 on Apr. 12, 2001 including U.S. application No. 10/089,900, claiming priority thereof.

Kaiser et al., PCT application No. PCT/US00/27418, published as WO 01/025747 on Apr. 12, 2001 including U.S. application No. 10/089,671, claiming priority thereof.

Keegan, *Applying Data Matrix Identification Symbols on Aerospace Parts*, NASA Technical Standard NASA–STD–6002, Jul. 2, 2001.

Keegan, *Application of Data Matrix Identification Symbols on Aerospace Parts Using Direct Part Marking Methods/Techniques*, NASA Technical Handbook NASA-H-DBK–6003, Jul. 2, 2001.

Co–Pending U.S. Appl. No. 09/716,625, filed Nov. 20, 2000.
Co–Pending U.S. Appl. No. 09/776,542, filed Jan. 19, 2001.
Co–Pending U.S. Appl. No. 10/006,782, filed May 12, 2001.
Co–Pending U.S. Appl. No. 29/144,321, filed Jun. 30, 2001.
Co–Pending U.S. Appl. No. 10/089,671, filed Apr. 02, 2002.
Co–Pending U.S. Appl. No. 10/089,900, filed Aug. 29, 2002.
Co–Pending U.S. Appl. No. 10/089,872, filed Sep. 16, 2002.
Co–Pending U.S. Appl. No. 10/089,870, filed Oct. 08, 2002.
Co–Pending U.S. Appl. No. 10/286,149, filed Nov. 01, 2002.
Co–Pending U.S. Appl. No. 10/306,923, filed Nov. 29, 2002.
Co–Pending U.S. Appl. No. 10/307,191, filed Nov. 29, 2002.
Co–Pending U.S. Appl. No. 10/321,873, filed Dec. 16, 2002.
Co–Pending U.S. Provisional Appl. No. 60/459,747, filed Apr. 01, 2003.
Co–Pending U.S. Provisional Appl. No. 60/518,577, filed Nov. 07, 2003.

* cited by examiner

Data format to be used in areas providing sufficient marking area for complete data content Data format to be used where marking area is insufficient to place a symbol containing complete data content.

XXXXX-XXXXXXXXXXXXXXXXXXXX-XXXXXXX        XXXXX*XXXXXXX

CAGE/NSCM    Part Number    Serial Number    CAGE/NSCM    Serial Number

Preferred symbol shape for narrow marking areas

14X14 Matrix Containing 13 Characters of Data

8X32 Matrix Containing 13 Characters of Data

FIG. 7

Additive Markings – Adhesive dispensing, Ink Jet, Laser Bonding, LENS, Liquid Metal Jet, Silk Screen, Stencil, and Thin Film Deposition Raised Markings – Cast, Forge, or Mold Recessed Markings – Cast, Forge, or Mold Textured Marking – Micro-Abrasive Blast Discolored Markings – Chemical Coloring, Electro-Chemical Coloring (AC) and Laser Coloring Etched Markings – Electro-Chemical Etch (DC) and Laser Etch Recessed Markings – Engraving and Milling Recessed Markings – Laser Engraving Recessed/Etched Marking Backfilled to Provide Contrast Impression Stamp Marking – Dot & LaserShot Peening Recessed Marking Coated to Prevent Accumulation of Foreign material or Corrosion Surface Coating Removed to Form Symbol

METHODS FOR IDENTIFICATION AND VERIFICATION USING DIGITAL EQUIVALENT DATA SYSTEM

REFERENCE TO RELATED APPLICATIONS

This application is a continuation-in-part from U.S. patent application Ser. No. 10/122,079, filed Apr. 12, 2002 the entire disclosure of which is incorporated herein by reference.

JOINT INVENTION OF GOVERNMENT EMPLOYEE AND NON-FEDERAL

PARTY OUTISDE OF ANY FUNDING AGEEMENT OR OTHER ARRANGEMENT

The invention described herein was made in part by an employee of the United States Government and may be manufactured and used by and for the Government of the United States for governmental purposes without the payment of any royalties thereon or therefor.

FIELD OF THE INVENTION

The invention generally relates to apparatus and methods for identification and verification. More particularly, the invention relates to apparatus and methods for detecting an element or elements extrinsically added to an object by using x-ray fluorescence. Even more particularly, the invention related to apparatus and methods for detecting an element extrinsically added to an object by using X-ray fluorescence to identify and authenticate that object.

BACKGROUND OF THE INVENTION

There has been significant interest in apparatus and methods for identifying and verifying various articles or products (or objects) such as explosives, ammunition, paint, petroleum products, and documents. Known methods used to identify and verify such objects generally involve adding and detecting materials like microparticles, bulk chemical substances, and radioactive substances. Similar marking methods include inks that are transparent in visible light are sometimes applied to objects and the presence (or absence) of the ink is revealed by ultraviolet or infrared fluorescence. Other methods include implanting microscopic additives that can be detected optically. Other methods used for identifying and verifying objects include those described in U.S. Pat. Nos. 6,106,021, 6,082,775, 6,030,657, 6,024,200, 6,007,744, 6,005,915, 5,849,590, 5,760,394, 5,677,187, 5,474,937, 5,301,044, 5,208,630, 5,057,268, 4,862,143, 4,485,308, 4,445,225, 4,390,452, 4,363,965, 4,136,778, and 4,045,676, as well as European Patent Application Nos. 0911626 and 0911627, the disclosures of which are incorporated herein by reference.

As well, there has been significant interest in using similar methods to collect and record data about an object. In particular there has been significant interest to authenticate objects using these methods, e.g. to prevent loss or counterfeiting. Recognizing that manual data collection and keyed data entry were inefficient and error-prone, many industries adopted bar code technology in the mid 1980s. Bar codes were determined, however, to not be suitable for direct part (or object) marking (DPM). Instead, bar codes were used on labels or other packaging for the object or part.

To obtain direct part marking, many industries-together with U.S. governmental agencies—developed machine-readable two-dimensional (2-D) symbols designed to be applied to non-paper substrates. This development resulted in the data matrix symbol technologies that could be permanently applied to the materials or substrate of most products or objects without impacting performance. Additional DPM technologies quickly followed and were adopted by the automotive, electronics, pharmaceutical, and aircraft industries. These industries relied heavily on the use of mold, cast, or forge; engraving; electrical arc pencil; electrical-chemical marking; embossing; hot stamp; rubber ink stamp; stencil and silk screen; vibration-etch; and add-on tags for part identification.

These marking methods, originally designed to apply human-readable markings, did not successfully apply micro-size ($1/32$-inch to $15/64$-inch square), high-density machine-readable symbols. Their manual operations also added to the large number of data transposition errors. Thus, industries began to refine existing marking methods so they could be utilized to apply 2-D (e.g., data matrix) symbols. The manual metal stamp, vibro-etch, and embossing technique methods were replaced by dot peen machines. Automated micro-profilers were designed to replace the manual cutting wheel used to produce paint stencils. Photo stencils and thermal printing materials were developed to replace the direct impact electro-chemical marking stencil materials. Ink jet and adhesive dispensing machines were built to replace rubber stamps. Laser marking systems were designed to replace the electric-arc etch and hot stamp processes. See, for example, "Applying Data Matrix Identification Symbols on Aerospace Parts" *NASA Technical Standard NASA-STD-6002A* (November 2002) and "Application of Data Matrix Identification Symbols to Aerospace Parts Using Direct Part Marking Methods/Techniques" *NASA Technical Handbook NASA-HDBK-6003A* (November 2002), the disclosures of which are incorporated herein by reference.

Unfortunately, many of the non-DPM methods for identifying and authenticating objects are unsatisfactory for several reasons. First, they are often difficult and time-consuming. In many instances, a sample of the object (of the object itself) must be sent to an off-site laboratory for analysis. In other instances, the apparatus are often expensive, large, and difficult to operate. Finally, due to the unsophisticated nature of the methods, they could be easily duplicated and counterfeited, rendering them useful only in the use of routine unsecured identification and not particularly useful for authentication.

Yet 2D (data matrix) symbols are also unsatisfactory. They can be limited to two-dimensional structures or are limited because of the type of substrate/material used in the object or product. Data matrix symbols for automatic identification have evolved to the point that optically visible marks, especially those that appear as checkerboard bar codes on parts, are possible on any surface. Many of those surfaces (especially highly polished or smooth reflective ones), however, are not friendly to the optical scanner used to capture the image of the symbol and decode it.

It is also common to mark data matrix symbols on the surface of an item and have them imaged even though the symbols have been covered with paint or other coatings. Reading those symbols through the paint/coating is generally accomplished by two methods. The first method requires the addition of some constituent that can be imaged by a sensor, e.g., a magneto-optic scanner that can sense and image a symbol that has been backfilled with a magnetic material. See, for example, U.S. Pat. No. 5,742,036, the disclosure of which is incorporated herein by reference. The second method requires changing the substrate when applying the symbol to the extent that symbol data cells are either significantly higher or lower than the host substrate, making them detectable with ultrasonic means. See, for example, U.S. Pat. No. 5,773,811, the disclosure of which is incorporated by reference.

Both methods offer the ability to detect symbols that are securely hidden under a coating of paint. These methods, however, do not offer uniqueness to the extent that the symbol precludes counterfeiting. As well, these symbols can be detected and marked on duplicate products almost as easily as visible marks, rendering them useful only in routine unsecured identification and not particularly useful for authentication purposes.

SUMMARY OF THE INVENTION

The invention provides apparatus and methods in which one or more elemental taggants that are extrinsically placed in an object are detected by x-ray fluorescence analysis to identify or authenticate the object. The taggant is manufactured as part of the object or the taggant is placed into a coating, packaging, label, or otherwise embedded onto the object for the purpose of later verifying the presence or absence of these elements by x-ray fluorescence. The taggant is then analyzed by XRF and the analysis is then converted into a 2D symbol format that can be used in various security applications. By using x-ray fluorescence analysis, the apparatus and methods of the invention are simple and easy to use, without the limitations experienced by current anti-counterfeiting technologies.

BRIEF DESCRIPTION OF THE DRAWINGS

FIGS. 1, 2a, 2b, 3, 4a, 4b, and 5–9 are views of one aspect of apparatus and methods according to the invention, in which:

FIG. 4a and 4b depict two aspects of the of the XRF apparatus of the invention;

FIGS. 1, 2a, 2b, 3, 4a, 4b, and 5–9 presented in conjunction with this description are views of only particular-rather than complete-portions of apparatus and methods according to the invention. Together with the following description, the Figures demonstrate and explain the principles of the invention.

DETAILED DESCRIPTION OF THE INVENTION

The following description provides specific details in order to provide a thorough understanding of the invention. The skilled artisan will understand, however, that the invention can be practiced without employing these specific details. Indeed, the invention can be practiced by modifying the illustrated apparatus and method and can be used in conjunction with apparatus and techniques conventionally used in the industry. For example, the invention is described with respect to apparatus and methods for identifying and tracking/tracing objects using taggants in combination with data matrix symbols. The invention described below, however, could be easily modified to be used in combination with any 2D symbols. Indeed, the invention could be modified to be used with any DPM technologies.

The invention uses x-ray fluorescence analysis to detect at least one elemental taggant that has been extrinsically added to an object. With x-ray fluorescence (XRF) analysis, x-rays produced from electron shifts in the inner shell(s) of atoms of the taggants and, therefore, are not affected by the form (chemical bonding) of the article being analyzed. The x-rays emitted from each element bear a specific and unique spectral signature, allowing one to determine whether that specific taggant is present in the product or article.

Figures 1, 2A, 2B:
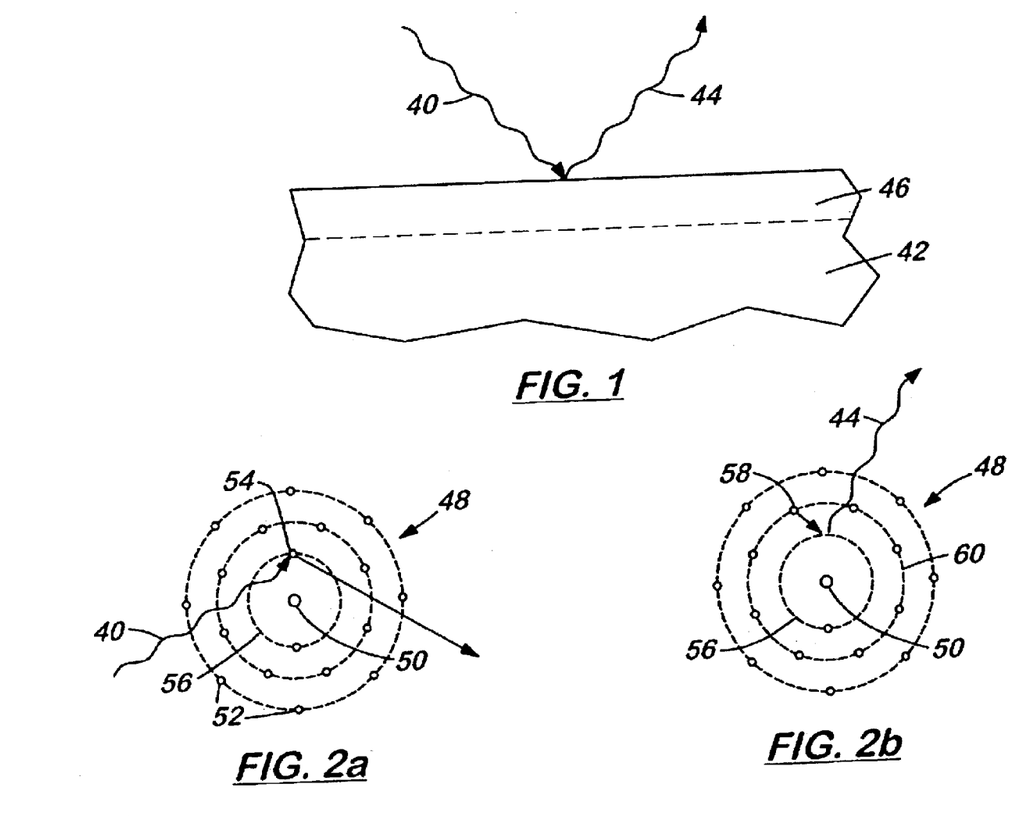
FIG. 1 generally depicts the operation of XRF.
FIG. 2a and 2b illustrate the operation of XRF at the molecular level.

FIGS. 1, 2a, and 2b represent how it is believed XRF generally operates. In FIG. 1, primary gamma rays or x-rays 40 are irradiated on a sample of a target material 46 of article 42. Secondary x-rays 44 are emitted from that sample of target material 46.

In FIGS. 2a and 2b, atom 48 of a taggant located within target material 46 has nucleus 50 surrounded by electrons 52 at discrete energy bands around the nucleus 50 (called electron shells). Each electron has a binding energy level equal to the amount of energy required to remove that electron from its corresponding shell. The innermost shell is the K shell, and has the highest binding energy levels associated with it. Electron 54 is located within K shell 56.

Primary x-ray or gamma ray photon 40 impacting atom 48 has a given energy. If that energy is greater than the binding energy level of K shell 56, the energy of x-ray photon 40 is absorbed by atom 48, and one of the electrons in K shell 56 (i.e., electron 54) is ejected. With a vacancy now in K shell 56 left by electron 54, atom 48 is energetic and unstable. To become more stable, that vacancy in K shell 56 can be—and usually is—filled by an electron located in a shell with a lower binding energy level, such as L-shell electron 58 in L shell 60. As L-shell electron 58 fills the vacancy in K shell 56, atom 48 emits a secondary x-ray photon 44. The energy levels (or corresponding wavelengths) of such secondary x-ray photons are uniquely characteristic to each elemental taggant, allowing the presence or absence of any specific taggant to be determined.

The at least one taggant employed in the invention can be any suitable taggant known in the art. See, for example, U.S. Pat. Nos. 5,474,937, 5,760,394, and 6,025,200, the disclosures of which are incorporated herein by reference. Suitable taggants include any element capable of being detected via XRF. The type of elements that can be used as the taggant are theoretically any of those listed in the periodic table, but the lower energy emitted by electrons in the lower atomic-number elements could be a limiting factor. Such lower energies can be re-absorbed much easier into its own material matrix or, in some cases, into the ambient atmosphere (e.g., air). Further, different isotopes of an element, as well as elements that "excite" only under certain conditions could be employed as the taggant in the invention. Example of taggants that could be used in the invention include any element with an atomic number ranging from 6 to 94.

The type of taggant depends, among other things, on the target object in which it is located. The material of the target object can interfere with the XRF detection because, as described below, backscattering and peaks emitted by the composition of the target object during XRF analysis can interfere with the taggant peaks. For example, if paper (as the target object) contained an As taggant and trace amounts of Pb existed in the paper, the K-level electrons of As and L-level electrons of Pb could give confusing readings during XRF detection. The type of the taggant also depends, in part, on the other anti-counterfeiting technology with which the invention is used.

In one aspect of the invention, the type of taggant should be selected based on the ability of the taggant and/or the substance in which it is located (i.e., a coating) to attach or bond to the target object. In many instances, the target object will be used, handled, and/or washed extensively. If the taggant (or the substance in which is located) is removed from the target object under such conditions, tagging the target object is of little value. For example, if a film or coating (e.g., ink) containing a taggant is applied to a target object (e.g., paper), the taggant and coating should be selected so that they will not be removed by the conditions to which the target object is periodically subjected (e.g., extensive contact with hands). Preferably, the coating and/or the taggant is selected in this aspect of the invention so that it chemically attaches or bonds to the target object, like paint attaches and bonds with a wall.

The amount and concentration of the taggant in the target object can also vary depending on the number of elements used and energy needed. The amount of taggant employed in the invention is determined by the minimum amount needed for XRF detection. Additional amounts of taggant can be used as described below. The concentration of the taggant is at least about 1 part per million (ppm), and can range from about 1–100 ppm. Larger taggant amounts can be used, but for economic reasons, a small amount is sufficient. Even lower taggant concentrations can be used (i.e., less than 1 ppm) as improved XRF devices and techniques become available.

Any suitable target object can be employed in the invention. Suitable target objects include those which the desired taggant(s) can be incorporated. Because XRF detection measures changes in the inner shell(s) of the taggant, it will not be significantly modified by chemical reactions that normally occur in the outer shells. Thus, it is possible to tag chemicals and have the taggant code be carried in any object manufactured with those chemicals. Target objects should be comprised of a material in which XRF detection is easy, e.g., little chance of background contamination, taggant deterioration, taggant destruction, contamination, or other deteriorating condition.

Suitable target objects include any manufactured goods or trade goods. Examples of manufactured goods include any of those goods listed in the 2000 and 3000 series of the SIC classification index. Examples of trade goods include any of those goods listed in the 5000 series of the SIC classification index. Examples of suitable target objects include machined automotive metal parts, formed appliance polymer parts, aircraft components, and/or aerospace components. In one aspect of the invention, the target object is an aircraft component such as a jet engine turbine blade or an aerospace component such as a Space Shuttle External Tank liquid hydrogen barrel panel.

In the invention, the at least one taggant can be incorporated into the target object in any suitable form. Suitable forms include those which place that taggant in the target object with little to no damage (either chemical or physical) to that object. See, for example, the description in U.S. Pat. Nos. 5,208,630, 5,760,394, and 6,030,657, the disclosures of which are incorporated herein by reference. Other suitable forms include using materials containing the taggant such as particulates like microparticles; solvents; coatings and films; adhesives; sprays; or a hybrid or combination of these methods. In any of these forms, the at least one taggant can be incorporated by itself or with another agent.

The at least one taggant can be incorporated in the target object using any suitable technique. Many existing tagging techniques involve the use of microparticles containing the elements, or compounds or compositions of the elements, comprising the at least one taggant. Additionally, particles can be manufactured wherein smaller particles, or compounds or compositions of the elements, containing the taggant. Such particles could be made of: magnetic or fluorescent materials to facilitate collection; refractory materials to enhance particle survival in an explosion; or chemically inert materials to enhance particle survival in a chemical reaction. Indeed, such particles could be made of non-durable, soluble, or reactive materials to enhance taggant dispersal in a fluid, aerosol, or powder system.

The taggant can be inserted into the target object of an article either during or after the article (or a part thereof) has been manufactured. During manufacture, the taggant can be incorporated into any location (including surfaces) of the article. Two (and three) dimensional shapes and patterns of the at least one taggant can be constructed using any desired combination of types and numbers of taggants.

The at least one taggant could also be incorporated after manufacture of the target object. The taggant could, for example, be incorporated into the already formed target object as a dopant. Additionally, the taggant can be implanted into the object or deposited as a coating or film on the object. As a coating or film, the taggant could be physically or chemically deposited by itself. The at least one taggant could also be incorporated as one ingredient (or contaminant) of another material (such as a mixture or solution) which forms a coating or film. In this aspect of the invention, the at least one taggant can be incorporated as an element or compound in solution (or suspension) with a liquid which is applied, such as by spraying, to the object. For example, the at least one taggant could be dissolved or suspended in a solvent so that when that solvent evaporates after being applied to the object, the residue left behind would contain the at least one taggant.

In one aspect of the invention, the method and apparatus of the invention can be used in place of 2D symbols (also referred to as "2D labels"). The conventional bar code symbol is "one-dimensional" in that the bars and spaces extend only in a single direction. To increase the information in machine-readable symbols, 2D labeling stores the information in two dimensions (i.e., a matrix) instead of a single dimension. See, for example, FIG. 7. Thus, the amount of information stored in the same amount of space can be increased more than 100 fold.

Most 2D labels are based on a wide range of technologies to both create the 2D labels, as well as to "read" the labels. 2D labels are usually created by modifying the surface of the object or product in some manner, including—but certainly not limited to—the following technologies: abrasive blast; adhesive dispensing; cast, forge or mold; dot peen; electro-chemical coating or etching; embroidery; engraving or milling; laser bonding or marking or peening; liquid metal jet; ink jet; silk screen; or stenciling (mechanical, laser, or photolithraphic). Using these methods, the surface of the object is modified to contain the two dimensional information.

The 2D labels are generally read using optical scanning techniques, such as scanning laser beams or CCD scanning.

The resulting electrical signals are then decoded to recover the data encoded in the symbols of the 2D label. Recent advances in 2D labeling techniques have allowed other types of techniques to be employed for detecting the information, including magneto-optic, ultrasound, infrared (thermal) imaging, capacitance, and radar. Such additional technologies have allowed the symbols in the 2D labels to be embedded beneath protective coating or within assemblies for security, aesthetic, and symbol-protection reasons. See, for example, the description in the brochure entitled *Innovative Technologies For Two-Dimensional Identification Coding* NASA Marshall Space Flight Center (Feb. 27, 2002), the disclosure of which is incorporated herein by reference.

The size needed for the 2D labels, however, is still quite large. Because of the method in which the 2D labels are made (using squares in a matrix) and detected, the matrix for the 2D labels is at least 0.25 square inches. Often, the size need is large, e.g., 0.5 to 1 square inch (or even more).

Figure 8:
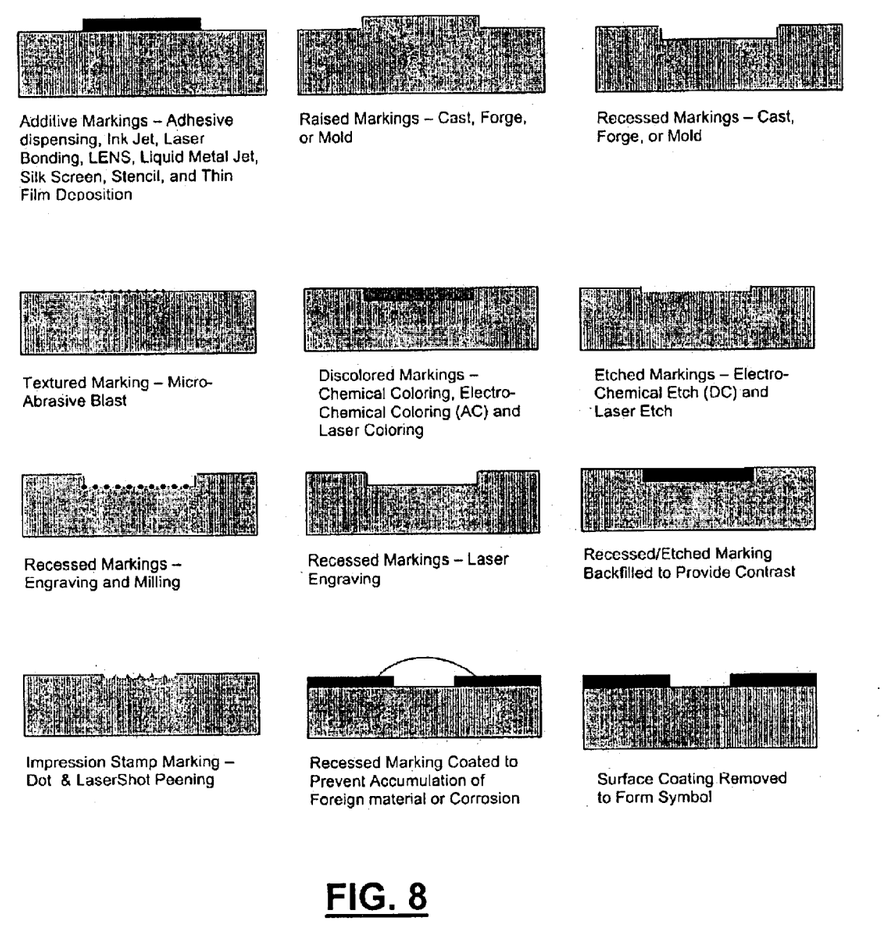

The invention exceeds the capabilities of the 2D labels in several aspects. First, the invention is able to identify and authenticate an object without having to modify the surface of the object. As noted above (and as illustrated in FIG. 8), current 2D labeling techniques modify the surface of the object in some manner to create the label. Using the taggant and XRF detection described herein, the invention need not modify the surface of the object at all.

As well, the invention is able to identify and track/trace on object without the need for the size required for 2D labeling techniques. As described above, 2D labeling techniques require a certain size on the object (generally 0.25 to 1 square inch). Using the taggants of the invention, such sizes are not required. Indeed, in one aspect of the invention, the sizes needed for the taggants of the invention can be on the microscopic level.

Figure 7:
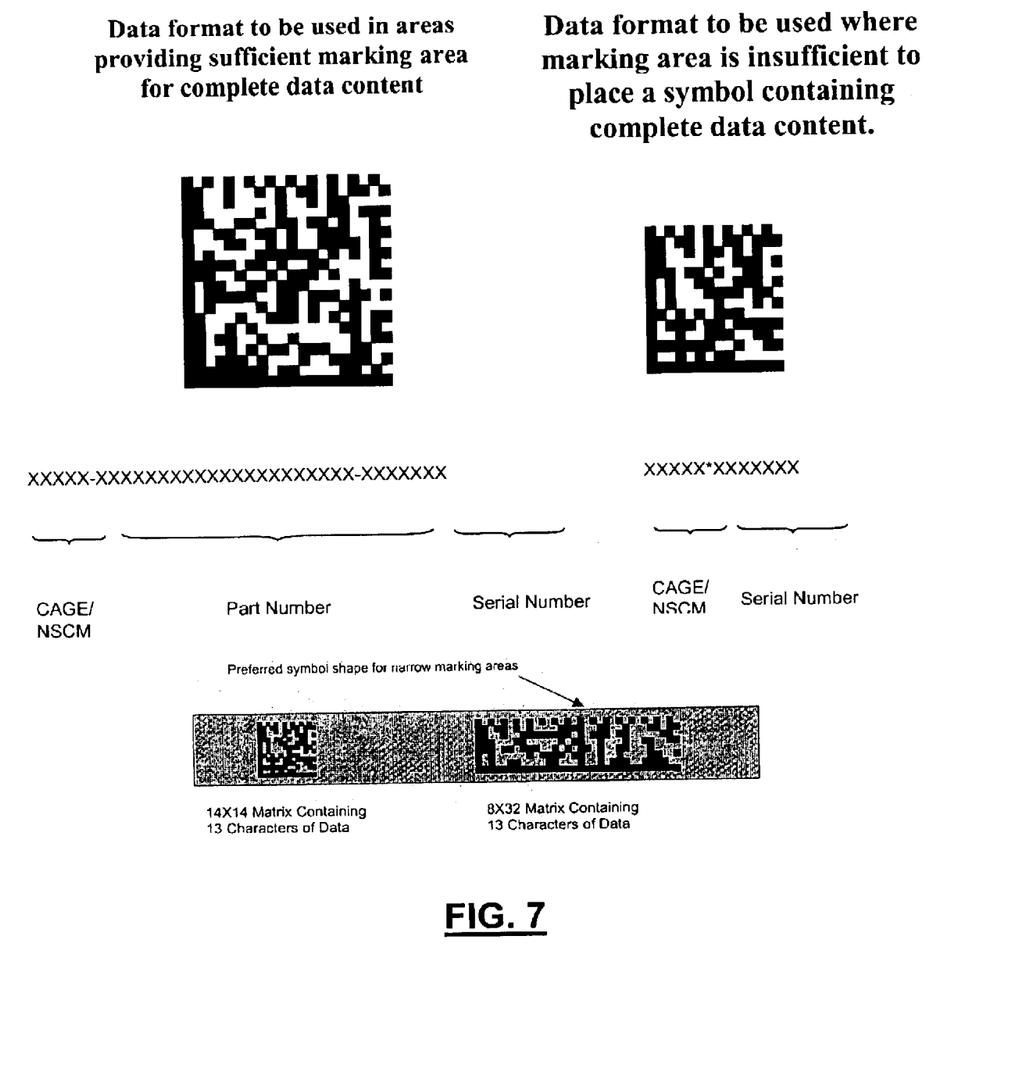
FIGS. 7 and 8 illustrate aspects of 2D symbols that can be used in one aspect of the invention.

The invention also is not limited to a "matrix" shape. 2D labeling techniques generally use information stored in a matrix form, as depicted in FIG. 7. The invention, however, is not so limited to this matrix form. Indeed, based on the manner in which the taggant is incorporated into the object as described above, the taggant can be present in any form or style in the object. Further, the invention is not limited to two dimensions, but can create a shape in three dimensions.

Further, 2D labeling techniques are highly dependent on the substrate in which the label is formed, e.g., type of material, surface roughness, geometry of surface, etc . . . . The invention, however, is not so limited to the substrate. Indeed, in most instances, the invention can be used with all types of substrates.

After the at least one taggant is present in the target object(s), the taggant(s) is detected to identify or verify the target material using XRF analysis as illustrated in FIG. 1. Primary x-rays 40 are used to excite a sample of the target material 46, and the secondary x-rays 44 that are emitted by the sample are detected and analyzed.

Figure 3:
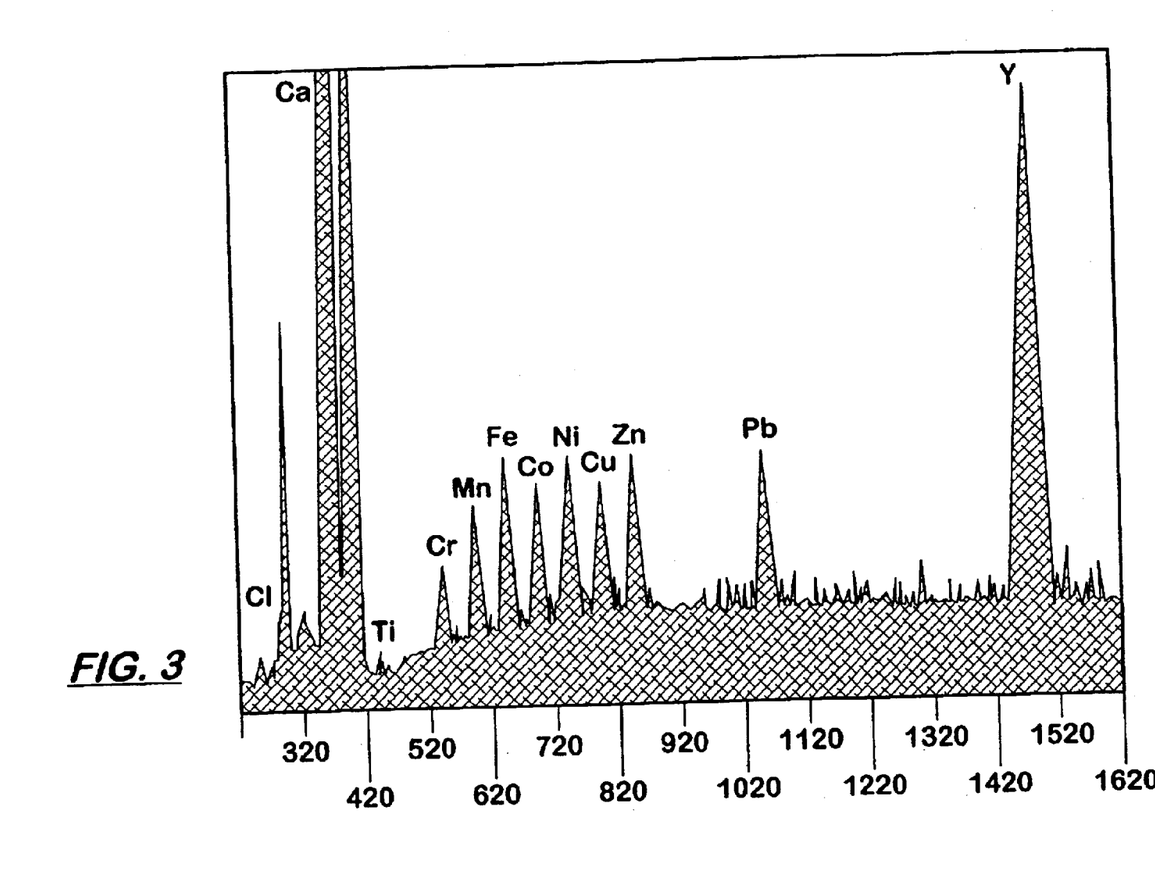
FIG. 3 shows an exemplary x-ray spectrum, e.g., for paper.

As shown in FIG. 3, the x-rays which are detected have various energies, e.g., there is a broad band of scattered x-rays with energies less than and greater than those of the exciting atom. FIG. 3 illustrates this spectrum for paper as the target object. Within this broad band, there are peaks due to the excitation of the taggant(s) in the sample. The ratio of the intensity of the radiation in any peak to the intensity of the background at the same energy (known as the peak-to-background ratio) is a measure of the concentration of the element which has characteristic X-rays at the energy of that peak, e.g., the taggant.

In one aspect of the detection method of the invention, at least one target object believing to contain known concentrations of the taggant(s) of interest is selected. The XRF analysis is performed on that target object (or a sample thereof) using a detection device or apparatus containing an x-ray radiation source ("source"), x-ray radiation detector ("detector"), support means, analyzer means, and calibration means.

Figure 4A:
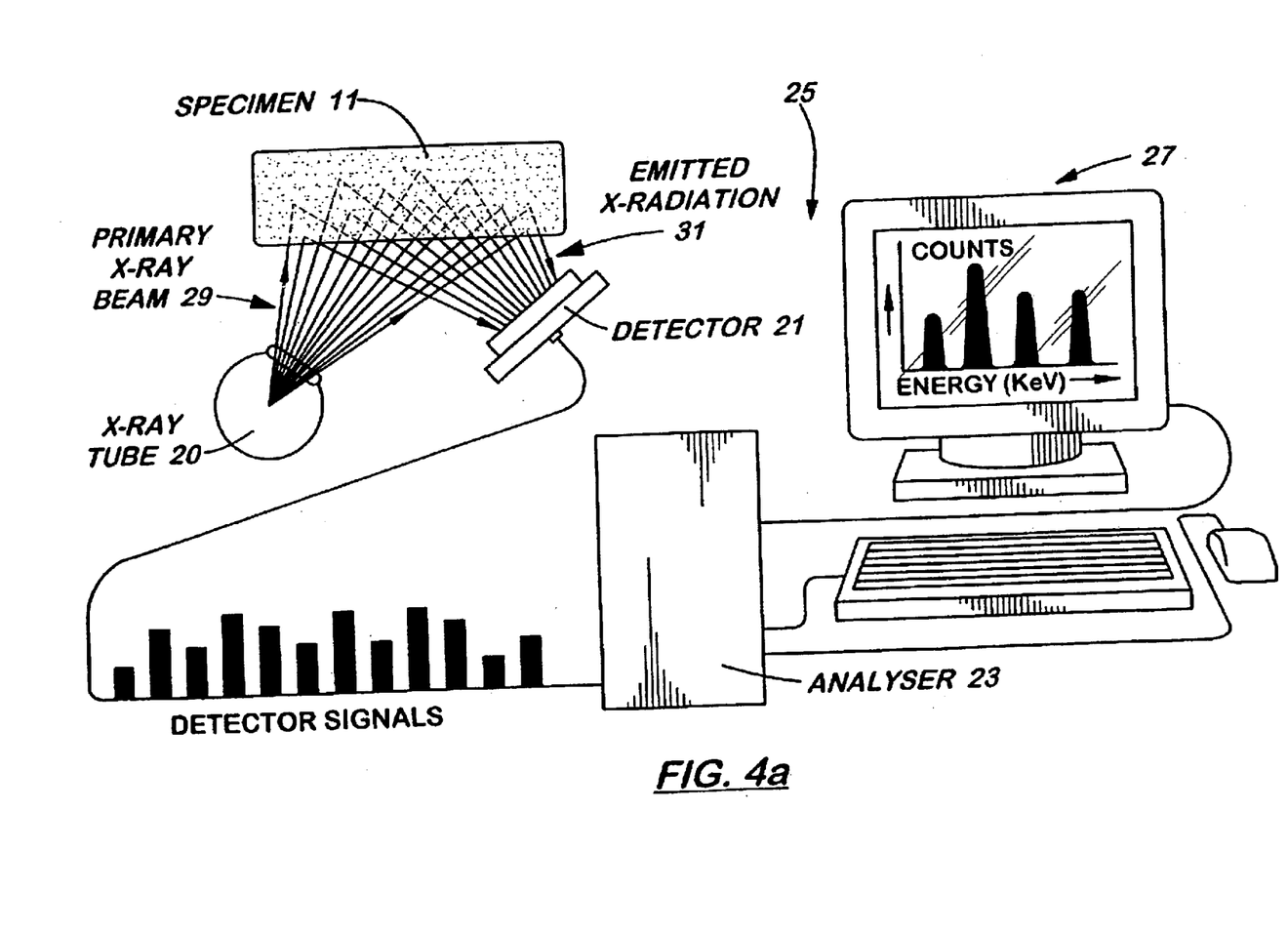

One aspect of the detection device of the invention is illustrated in FIG. 4a. In this Figure, the detection apparatus 25 has an ordinary x-ray fluorescence spectrometer capable of detecting elements present in a coating, package or material. X-rays 29 from a source (e.g., either x-ray tube or radioactive isotope) 20 impinge on a sample 11 which absorbs the radiation and emits x-rays 31 to an x-ray detector 21 and analyzer 23 capable of energy or wavelength discrimination. This is accomplished by using a commercially available x-ray spectrometer such as an Edax DX-95 or a MAP-4 portable analyzer, commercially available from Edax Inc., Mahwah, N.J. Part of analyzer 23 includes a computerized system 27.

Figure 4B:
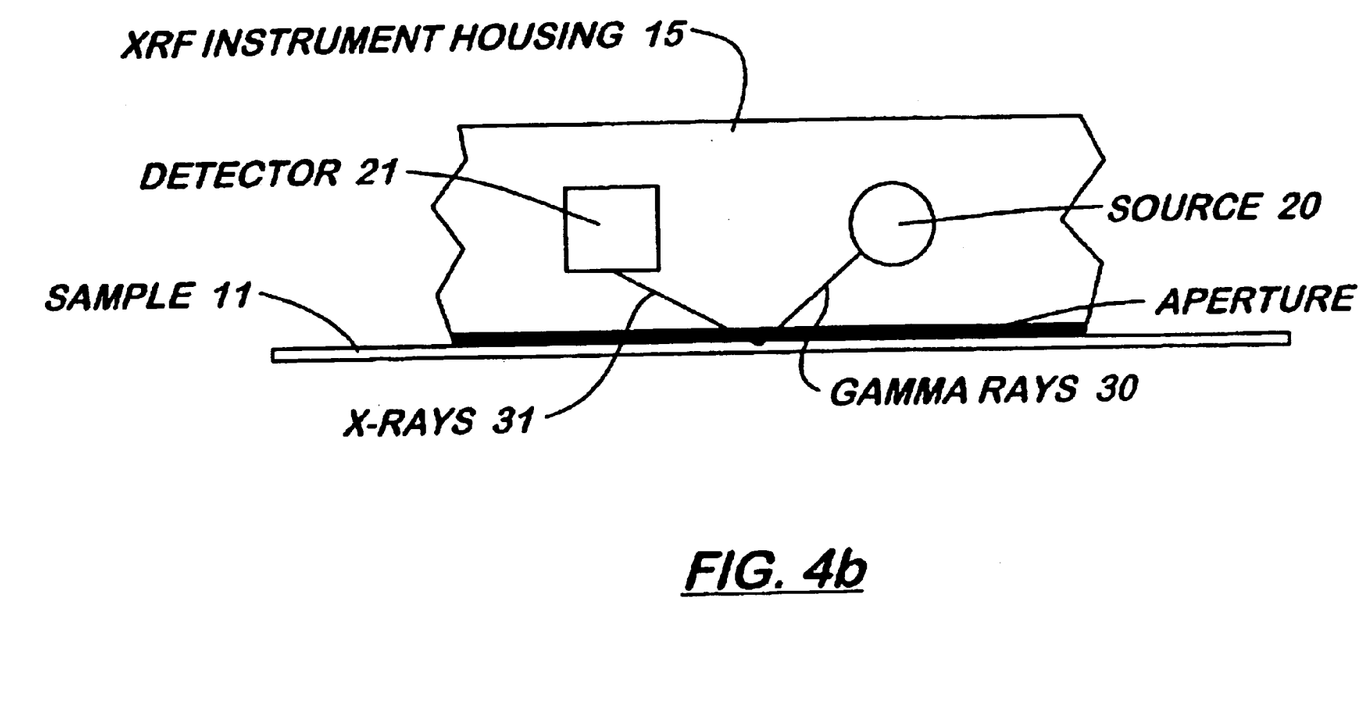

Another aspect of the detection apparatus of the invention is illustrated in FIG. 4b. In this Figure, the detection apparatus 25 has an instrument housing 15 which contains the various components. Gamma rays or x-rays 30 from a source (e.g., either x-ray tube or radioactive isotope) 20 are optionally focused by aperture 10 to impinge on a sample 11. Sample 11 contains the at least one taggant which absorbs the radiation and emits x-rays 31 to an x-ray detector 21. Optionally, analyzing means can be incorporated within housing 15.

The invention, however, is not limited to the detection apparatus depicted in FIGS. 4a and 4b. Any suitable source, or plurality of sources, known in the art can be used as the source in the detection device of the present. See, for example, U.S. Pat. Nos. 4,862,143, 4,045,676, and 6,005,915, the disclosures of which are incorporated herein by reference. During the XRF detection process, the source bombards the taggant with a high energy beam. The beam may be an electron beam or electromagnetic radiation such as X-rays or gamma rays. The source, therefore, may be any material that emits such high energy beams. Typically, these have been x-ray emitting devices such as x-ray tubes or radioactive sources.

To target, the beam can be focused and directed properly by any suitable means such as an orifice or an aperture. The configuration (size, length, diameter . . . ) of the beam should be controlled, as known in the art, to obtain the desired XRF detection. The power (or energy level) of the source should also be controlled, as known in the art, to obtain the desired XRF detection.

The source(s) can be shielded and emit radiation in a space limited by the shape of the shield. Thus, the presence, configuration, and the material used for shielding the source should be controlled for consistent XRF detection. Any suitable material and configuration for that shield known in the art can be employed in the invention. Preferably, any high-density materials used as the material for the shield, e.g., tungsten or brass.

Any suitable detector, or plurality of detectors, known in the art can be used as the detector in the detection device of the invention. See, for example, U.S. Pat. Nos. 4,862,143, 4,045,676, and 6,005,915, the disclosures of which are incorporated herein by reference. Any type of material capable of detecting the photons omitted by the taggant may be used. Silicon and CZT (cadmium-zinc-telluride) detectors have been conventionally used, but others such as proportional counters, germanium detectors, or mercuric iodide crystals can be used.

Several aspects of the detector should be controlled to obtain the desired XRF detection. First, the geometry between the detector and the target material should be controlled. The XRF detection also depend on the presence, configuration, and material—such as tungsten and beryllium—used as a window to allow x-rays photons to strike the detector. The age of the detector, voltage, humidity, variations in exposure, and temperature can also impact the XRF detection and, therefore, these conditions should be controlled.

The analyzer means sorts the radiation detected by the detector into one or more energy bands and measures its intensity. Thus, any analyzer means performing this function could be used in the invention. The analyzer means can be a multi-channel analyzer for measurements of the detected radiation in the characteristic band and any other bands necessary to compute the value of the characteristic radiation as distinct from the scattered or background radiation. See, for example, U.S. Pat. Nos. 4,862,143, 4,045,676, and 6,005,915, the disclosures of which are incorporated herein by reference.

The XRF also depends on the resolution of the x-rays. Background and other noise must be filtered from the x-rays for proper measurement, e.g., the signals must be separated into the proper number of channels and excess noise removed. The resolution can be improved by cooling the detector using a thermoelectric cooler—such as a nitrogen or a peltier cooler—and/or by filtering. Another way to improve this resolution is to use pre-amplifiers.

The support means supports the source and detector in predetermined positions relatively to a sample of the target material to be irradiated. Thus, any support means performing this function could be used in the invention. In one example, the support means comprises two housings, where the source and detector are mounted in a first housing which is connected by a flexible cable to a second housing in which the analyzer means is positioned as illustrated in FIG. 4a. If desired, the first housing may then be adapted to be hand-held. In another example, the source and detector as well as the other components of the detection device are mounted in a single housing as illustrated in FIG. 4b.

The calibration means are used to calibrate the detection apparatus, thus insuring accuracy of the XRF analysis. In this calibration, the various parameters that could be modified and effect the measurement are isolated and calibrated. For example, the geometrical conditions or arrangements can be isolated and calibrated. In another example, the material matrix are isolated and calibrated. Preferably, internal (in situ) calibration during detection is employed as the calibration means in the invention. Components, such as tungsten shielding, are already present to internally calibrate during the XRF analysis. Other methods, such as fluorescence peak or Compton backscattering, could be used for internal calibration in the invention.

Analyzer means, which includes a computerized system 27, is coupled to, receives, and processes the output signals produced by detector 21. The energy range of interest, which includes the energy levels of the secondary x-ray photons 44 emitted by the taggant(s), is divided into several energy subranges. Computerized system 27 maintains counts of the number of X-ray photons detected within each subrange using specific software programs, such as those to analyze the detection and x-ray interaction and to analyze backscatter data. After the desired exposure time, computerized system 27 with display menus stops receiving and processing output signals and produces a graph of the counts associated with each subrange.

Figure 6:
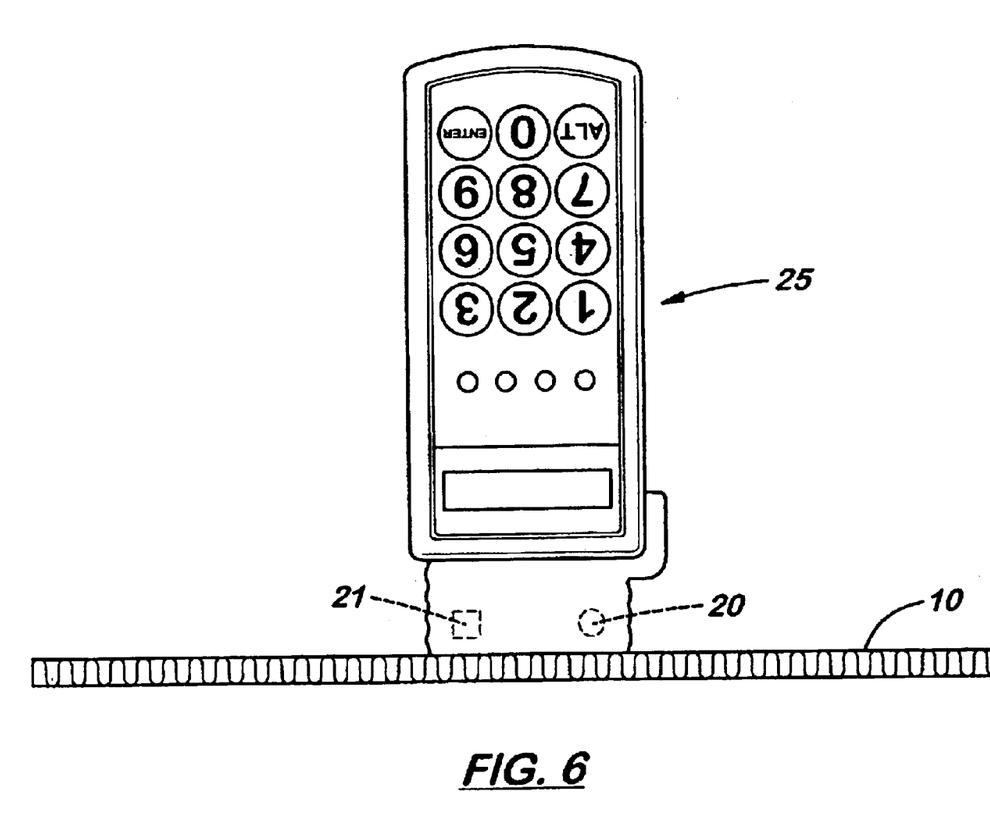
FIG. 6 shows another aspect of the XRF apparatus of the invention.

FIG. 6 illustrates another apparatus and detection method according to the invention. In this Figure, detection apparatus 25 is capable of detecting at least one taggant present in target material 10, such as a document. Detection apparatus 25 is a portable device that can be small enough to be hand-held. Detection apparatus 25 contains all the components discussed above (i.e., source, detector, analyzer means, and calibration means) in a single housing, thus allowing the portability and smaller size.

Figure 5:
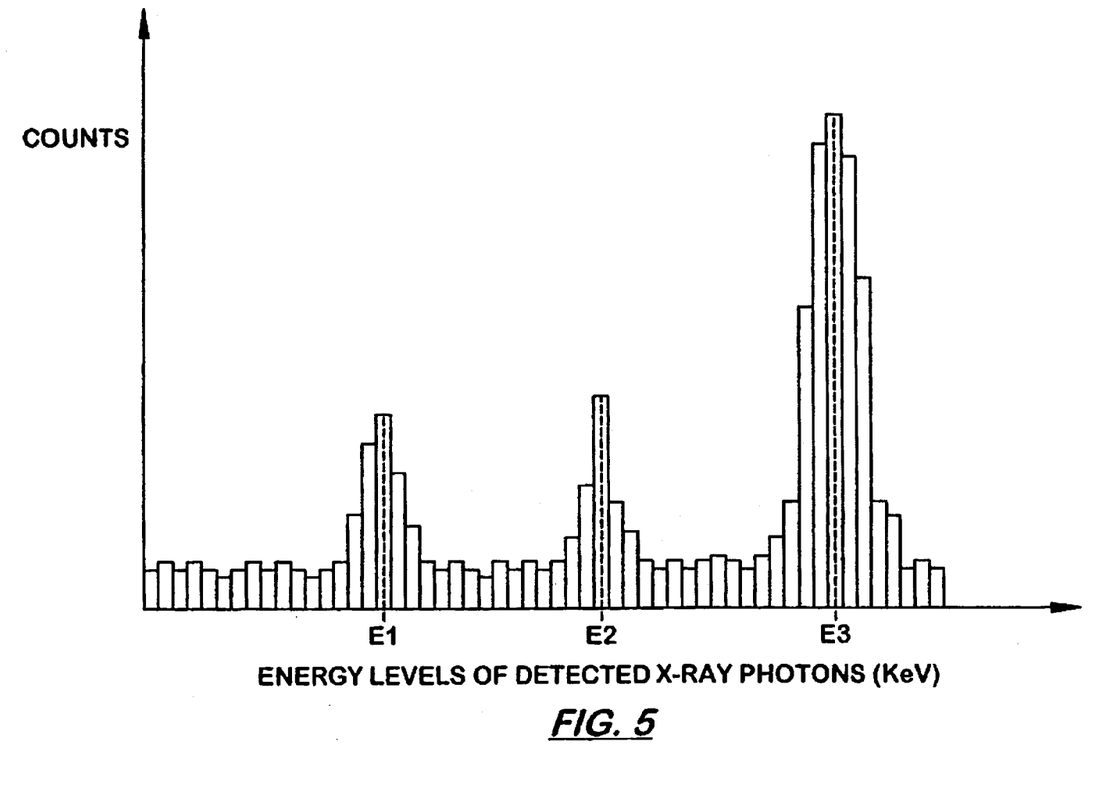
FIG. 5 illustrates exemplary energy levels of x-rays in an x-ray spectrum.

FIG. 5 is a representative graph of the counts associated with each subrange. This graph is essentially a histogram representing the frequency distribution of the energy levels E1, E2, and E3 of the detected x-ray photons. Peaks in the frequency distribution (i.e., relatively high numbers of counts) occur at energy levels of scattered primary x-ray photons as well as the secondary x-ray photons from the taggant(s). A primary x-ray photon incident upon a target material may be absorbed or scattered. The desired secondary x-ray photons are emitted only when the primary x-ray photons are absorbed. The scattered primary x-ray photons reaching the detector of the system create an unwanted background intensity level. Accordingly, the sensitivity of XRF analysis is dependent on the background intensity level, and the sensitivity of XRF detection may be improved by reducing the amount of scattered primary x-ray photons reaching the detector. The peak occurring at energy levels of scattered primary x-ray photons is basically ignored, while the other peaks—those occurring at E1, E2, and E3—are used to identify the at least one taggant present in the target object.

As depicted in FIG. 5, in one aspect of the invention the XRF analysis can result in a spectral data output (SDO) in a graphical format. In this aspect, the invention can establish a relationship between the SDO and the 2D symbol format (e.g., the Data Matrix format). Indeed, the invention is able to convert the unique XRF characteristics of an XRF SDO to a 2D symbol format. Often, the 2D symbol is consistent with a given standard, such as the NASA-STD-6002A format and can be used in various security and authentication applications.

In many instances, industries have a standard for identifying objects by direct part marking. For example, as illustrated in FIG. 7, there is a baseline convention for assigning identification to aerospace parts (e.g., NASA-STD-6002A standard). While such standards make identification of these objects easy throughout the industry, they suffer form the limitations mentioned above that exist with 2D symbols. By using XRF analysis and then converting the SDO to the 2D symbols, such limitations are no longer present.

Figure 9:
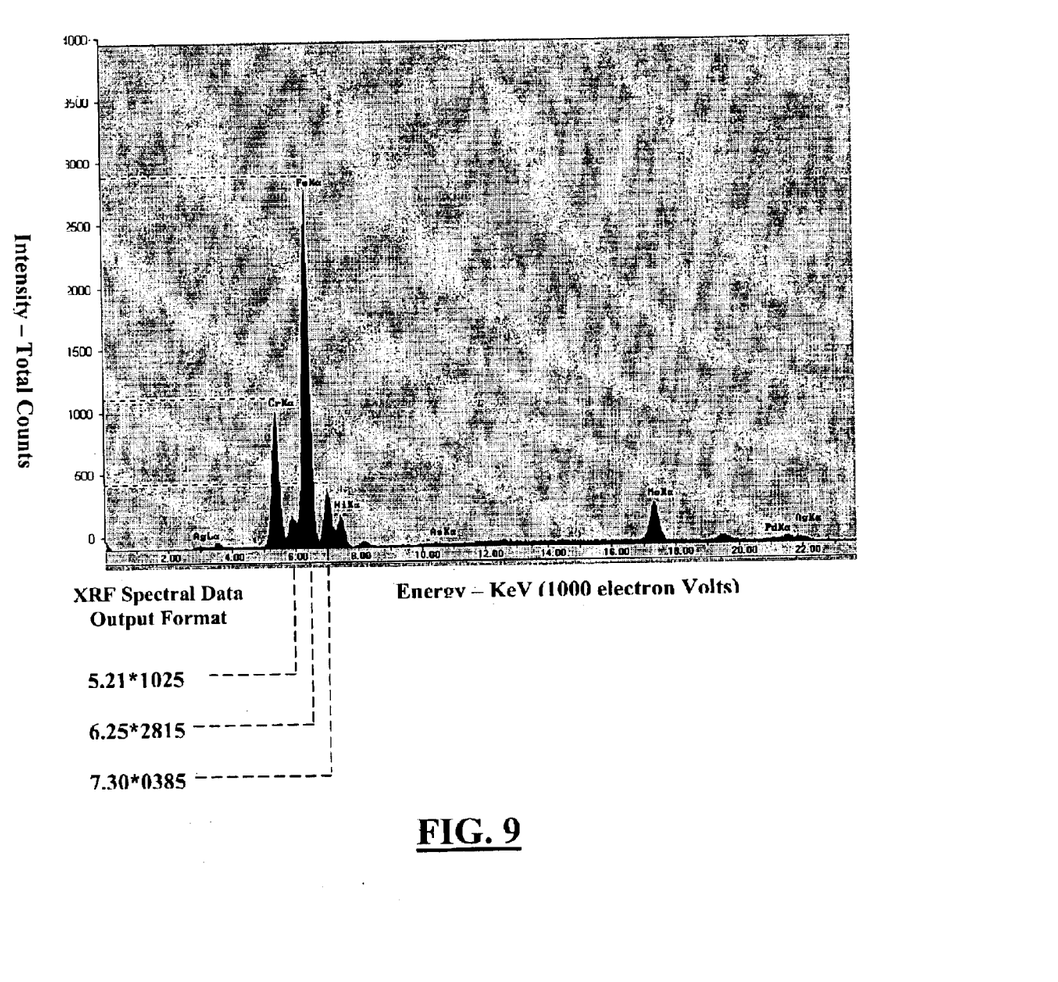
FIG. 9 illustrates a method of converting an XRF analysis to a 2D symbol in one aspect of the invention.

FIG. 9 illustrates a typical XRF SDO and how it can be converted to data matrix symbols. Of course, this conversion could be adapted to bar codes, Data Matrix codes and other 2D symbols, as well as other DPM technologies. In the aspect of the invention depicted in FIG. 9, the data from an XRF SDO is first converted to an ASCII character set or code. As described above, each element in the periodic table fluoresces characteristic K and L shell energies when energized by XRF. These energies are then assigned a respective location on the X-axis. When the location on the X-axis is assigned for a particular element, a value is also assigned numerically to represent that element consistent with its location on the X-axis. Thus, a particular element will always have the same location on the X-axis, will be represented by the same numeric value associated with that location, and will correlate to the same members of the ASCII character set.

The concentration or amount of the element contained in any given object energizes a known photon count per second and this value is shown along the Y-axis. When the location (concentration) on the Y-axis is assigned (or intentionally formulated) with a particular element, a value is also assigned numerically to represent that element consistent with its expected or intended location on the Y-axis. Thus, a particular elemental concentration will always have the same location on the Y-axis, will be represented by the same numeric value associated with that location, and will correlate to the same member of the ASCII character set. Accordingly, a particular element's identification is translated from SDO values (recognized only by XRF) to ASCII characters in alphanumeric form (recognized by humans) and then to 2D symbol format with 0's and 1's (recognized by computers).

This invention provides a means for these values on the X-axis (elemental location) and the Y-axis (elemental concentration) to be expressed numerically or alphanumerically in the ASCII character code. Any single element with a given concentration has a particular combination of X-axis location and Y-axis and its identification can therefore represent a particular ASCII character. Additional elements with a particular concentration have their own respective locations on the X-axis and concentrations on the Y-axis and can, therefore, represent other ASCII characters. When the various elements and their concentrations are combined as a set, they form a defined string of characters that correlate exactly with the alphanumeric assigned CAGE, part number or serial number that is commonly used to establish the identity of an object.

Then, these ASCII characters can be used to form identification conventions that are compatible with the existing part marking codes, e.g., 2D symbols. Using commercially available software conversion routines (i.e., those available from the Automated Identification Manufacturers organization), ASCII characters can easily encoded into linear bar codes, 2D codes such as Data Matrix symbols, and other symbols. For example, the ASCII characters derived from SDO values exemplified in FIG. 9 can be converted to a corresponding data matrix symbol, recognized by standards for part identification where direct part marking is an advantage. Below is one illustration of a single element SDO values from FIG. 9 converted to ASCII characters and then to a 2D symbol.

5.21*1025=>▨

Below is another illustration where of a mixture of elements with their own respective locations on the X-axis and concentrations on the Y-axis (representing multiple ASCII characters as a set) can form a defined string of characters that correlate exactly with the alphanumeric assigned CAGE (e.g. one that is commonly used to establish the identity of a manufacturer or provider). Longer naming conventions such as part numbers and serial numbers can be arranged in a similar manner.

5.21*1025×6.25*2815×10.33*0999×4.22*1899=>CAGE▨

In another aspect of the invention, the XRF SDO of the host substrate could be an additional verification/authentication/identification set of information that would compose the total identity of the item. In this aspect of the invention, the elemental taggant added to the substrate would comprise one identification means while the XRF SDO of the substrate material adjacent to the elemental taggant could be used in concert with the elemental taggant to form a more complete verification of the authenticity of the object in question. If used in conjunction with standard DPM symbols that denotes the common identity of the object in question, the three sets of information could comprise a unique set of identifiers that would be impossible to duplicate, thereby authenticating the object when the three sets of information are present.

In this aspect of the invention, all sets of identification means can be expressed in ASCII format. The computer would take the sets of information and immediately verify presence or absence of common and unique features. The computer database would compare these sets of information to those entered at the time the part or object was first manufactured when these marks, taggants, and other means of identification were extrinsically added or intrinsically registered. The comparison and successful detection of all known forms of identification relative to that part or object would determine authenticity. The absence of unique forms of identification, such as the elemental taggant, the elemental taggant in the concentrations first applied, or a matching substrate material would raise concern that the part or object is counterfeit or misidentified in some other way. Authenticity would only be assured if all conditions at the time of evaluation matched the conditions in the entered in the database at the time of manufacture.

Once having the all aspects of extrinsically added DPM symbols, extrinsically added elemental taggants, and the intrinsic constituents of the substrate material converted to ASCII characters and then encoded into conventions such as a data matrix symbol, any suitable method can be used to identify the object. In one aspect of the invention, a database can be built to facilitate this conversion process. This database would contain the known taggants, their corresponding ASCII codes, as well as the corresponding data matrix symbol. This database would then be stored as part of the software in an XRF device. Thus, when analyzing an object, the XRF device would automatically convert the SDO output into the desired data matrix symbol.

Thus, the apparatus and method of the invention can identify an object or article once it has been tagged. The ability to invisibly tag an article and read the tag as a data matrix symbol provides an invaluable asset in any industry that authenticates, verifies, tracks, labels, or distributes goods of any kind, and could further prevent copying and counterfeiting of goods.

The process of authentication would be facilitated through two means. First, the ASCII conversion of XRF SDO values to encoded conventions such as 2D symbols could standardize XRF SDO value expressions. Second, it would enable all identification conventions inherent to the invention to be communicated through well established networks without any other computer in the network having to know the difference between an XRF SDO for an elemental taggant, a 2D symbol marked directly on a part or a bar code on a label. Since the process of authentication involves determining that the object in question has exactly the same characteristics as an object previously determined as the original, unique characteristics such as elemental taggants can work together with communication networks, making conversions to standardized conventions a part of the process for authentication.

Having described the preferred aspects of the invention, it is understood that the invention defined by the appended claims is not to be limited by particular details set forth in the above description, as many apparent variations thereof are possible without departing from the spirit or scope thereof.

We claim:

1. A method for authenticating an object, comprising:
   placing a taggant in a portion of an object;
   causing the taggant to radiate an x-ray that penetrates through the portion of the object;
   analyzing through that portion whether the x-ray has a specific energy signature; and
   converting that energy signature into a portion of a direct part marking symbol.

2. The method of claim 1, wherein the direct part marking symbol is a 2D symbol.

3. The method of claim 1, wherein the object is an aerospace part.

4. The method of claim 1, wherein the energy signature is converted into an ASCII character code.

5. The method of claim 4, further comprising converting the ASCII character code into the portion of the direct part marking symbol.

6. A method for tracking an object, comprising:
   placing a taggant in a portion of an object;
   causing the taggant to radiate an x-ray that penetrates through the portion of the object;
   analyzing through that portion whether the x-ray has a specific energy signature; and
   converting that energy signature into a portion of a direct part marking symbol.

7. The method of claim 6, wherein the direct part marking symbol is a 2D symbol.

8. The method of claim 6, wherein the object is an aerospace part.

9. The method of claim 6, wherein the energy signature is converted into an ASCII character code.

10. The method of claim 9, further comprising converting the ASCII character code into the portion of the direct part marking symbol.

11. A method for authenticating an object, comprising:
    placing a taggant in a portion of an object;
    impinging an x-ray on the taggant to cause the taggant to radiate an x-ray;
    analyzing whether the x-ray has a specific energy signature; and
    converting that energy signature into a portion of a 2D symbol.

12. The method of claim 11, wherein the object is an aerospace part.

13. The method of claim 11, wherein the energy signature is converted into an ASCII character code and then from the ASCII character code into the portion of the 2D symbol.

14. The method of 11, wherein there is a plurality of taggants and the energy signatures from the plurality forms the 2D symbol.

15. An x-ray fluorescence device, comprising
    an x-ray source;
    an x-ray detector; and
    means for converting an x-ray energy signature into a portion of a direct part marking symbol.

16. The device of claim 15, wherein the direct part marking symbol is a 2D symbol.

17. The device of claim 15, wherein the converting means changes the energy signature into an ASCII character code.

18. The device of claim 17, wherein the converting means changes the ASCII character code into the portion of the direct part marking symbol.

19. The device of claim 15, wherein the converting means comprises a database of ASCII character codes corresponding to known elemental x-ray signatures.

20. The device of claim 19, wherein the converting means comprises a database of direct part marking symbols corresponding to ASCII character codes.

21. An authentification system containing an x-ray fluorescence device, the device comprising:
    an x-ray source;
    an x-ray detector; and
    means for converting an x-ray energy signature into a portion of a direct part marking symbol.

22. The system of claim 21, wherein the converting means changes the energy signature into an ASCII character code and the converting means changes the ASCII character code into the portion of the direct part marking symbol.

* * * * *